(12) United States Patent
Mayer et al.

(10) Patent No.: US 10,939,900 B2
(45) Date of Patent: *Mar. 9, 2021

(54) SUTURE ANCHOR AND METHOD FOR FIXATING A SUTURE RELATIVE TO HARD TISSUE

(71) Applicant: SportWelding GmbH, Schlieren (CH)

(72) Inventors: Jörg Mayer, Niederlenz (CH); Andrea Müller, Winterthur (CH); Mario Lehmann, Les Pommerats (CH); Stephanie Goebel-Mehl, Mettmenstetten (CH); Milica Berra, Schlieren (CH); Andreas Wenger, Muri b. Bern (CH)

(73) Assignee: SPORTWELDING GMBH, Schlieren (CH)

( * ) Notice: Subject to any disclaimer, the term of this patent is extended or adjusted under 35 U.S.C. 154(b) by 449 days.

This patent is subject to a terminal disclaimer.

(21) Appl. No.: 15/460,330

(22) Filed: Mar. 16, 2017

(65) Prior Publication Data
US 2017/0181742 A1    Jun. 29, 2017

Related U.S. Application Data

(62) Division of application No. 13/239,460, filed on Sep. 22, 2011, now Pat. No. 9,615,820.
(Continued)

(51) Int. Cl.
*A61B 17/04*    (2006.01)
*A61B 17/00*    (2006.01)

(52) U.S. Cl.
CPC ...... *A61B 17/0401* (2013.01); *A61B 17/0469* (2013.01); *A61B 2017/00831* (2013.01);
(Continued)

(58) Field of Classification Search
CPC .............................................. A61B 2017/0456
See application file for complete search history.

(56) References Cited

U.S. PATENT DOCUMENTS 5,100,417 A * 3/1992 Cerier ................ A61B 17/0401
606/139
5,464,427 A    11/1995 Curtis et al.
(Continued)

FOREIGN PATENT DOCUMENTS

CN    201286881    8/2009
EP    2221014    8/2010
(Continued)

OTHER PUBLICATIONS

Chinese Office Action dated Jan. 2, 2020, Application No. 201710472790.7; English translation included; 17 pages.
(Continued)

*Primary Examiner* — Shaun L David
(74) *Attorney, Agent, or Firm* — Rankin, Hill & Clark LLP (57) ABSTRACT

A suture anchor includes a material having thermoplastic properties and is fixated in a hard tissue opening by liquefying at least part of this material and letting it penetrate into walls of the hard tissue opening. During the named fixation and preferably towards the end of it, the suture being held in a distal suture conduit is locked relative to the hard tissue by being clamped between the suture anchor and the wall of the hard tissue opening or by being clamped or braked through collapse of the suture conduit.

7 Claims, 5 Drawing Sheets

Related U.S. Application Data (60) Provisional application No. 61/386,160, filed on Sep. 24, 2010, provisional application No. 61/437,227, filed on Jan. 28, 2011.

(52) U.S. Cl.
CPC ........... *A61B 2017/00955* (2013.01); *A61B 2017/042* (2013.01); *A61B 2017/0409* (2013.01); *A61B 2017/0414* (2013.01); *A61B 2017/0417* (2013.01); *A61B 2017/0419* (2013.01); *A61B 2017/0424* (2013.01); *A61B 2017/0446* (2013.01); *A61B 2017/0496* (2013.01)

(56) References Cited

U.S. PATENT DOCUMENTS

| | | |
|---|---|---|
| 5,486,197 A | 1/1996 | Le et al. |
| 5,522,844 A | 6/1996 | Johnson |
| 5,709,708 A | 1/1998 | Thal |
| 5,718,717 A * | 2/1998 | Bonutti .............. A61B 17/0401 606/139 |
| 5,733,307 A | 3/1998 | Dinsdale |
| 5,891,168 A | 4/1999 | Thal |
| 5,941,901 A | 8/1999 | Egan |
| 5,993,458 A * | 11/1999 | Vaitekunas ........ A61B 17/0401 606/104 |
| 6,024,758 A | 2/2000 | Thal |
| 6,214,031 B1 | 4/2001 | Schmieding et al. |
| 6,319,270 B1 | 11/2001 | Grafton et al. |
| 6,508,830 B2 | 1/2003 | Steiner |
| 6,511,499 B2 | 1/2003 | Schmieding et al. |
| 6,517,564 B1 | 2/2003 | Grafton et al. |
| 6,544,281 B2 | 4/2003 | ElAttrache et al. |
| 6,569,188 B2 | 5/2003 | Grafton et al. |
| 6,620,185 B1 | 9/2003 | Harvie et al. |
| 6,641,596 B1 | 11/2003 | Lizardi |
| 6,641,597 B2 | 11/2003 | Burkhart et al. |
| 7,008,226 B2 | 3/2006 | Mayer et al. |
| 7,172,420 B2 | 2/2007 | Huguenin et al. |
| 7,211,088 B2 | 5/2007 | Grafton et al. |
| 7,226,469 B2 | 6/2007 | Benavitz et al. |
| 7,329,272 B2 | 2/2008 | Burkhart et al. |
| 7,335,205 B2 | 2/2008 | Aeschlimann et al. |
| 7,429,266 B2 * | 9/2008 | Bonutti .................. B29C 66/69 606/232 |
| 7,442,202 B2 | 10/2008 | Dreyfuss |
| 7,491,217 B1 * | 2/2009 | Hendren ............ A61B 17/0401 606/232 |
| 7,585,311 B2 | 9/2009 | Green et al. |
| 7,678,134 B2 | 3/2010 | Schmieding et al. |
| 7,695,495 B2 | 4/2010 | Dreyfuss |
| 7,785,347 B2 | 8/2010 | Harvie et al. |
| 8,409,251 B2 | 4/2013 | Cooper et al. |
| 9,615,820 B2 | 4/2017 | Mayer et al. |
| 2004/0068267 A1 | 4/2004 | Harvie et al. |
| 2005/0222575 A1 | 10/2005 | Ciccone et al. |
| 2005/0222618 A1 | 10/2005 | Dreyfuss et al. |
| 2005/0222619 A1 | 10/2005 | Dreyfuss et al. |
| 2006/0105295 A1 | 5/2006 | Mayer et al. |
| 2006/0149280 A1 | 7/2006 | Harvie et al. |
| 2006/0161159 A1 | 7/2006 | Dreyfuss et al. |
| 2006/0253119 A1 * | 11/2006 | Berberich .......... A61B 17/0401 606/232 |
| 2007/0060922 A1 | 3/2007 | Dreyfuss |
| 2007/0073299 A1 | 3/2007 | Dreyfuss et al. |
| 2007/0135841 A1 | 6/2007 | Dreyfuss |
| 2007/0185494 A1 | 8/2007 | Reese |
| 2007/0288027 A1 | 12/2007 | Grafton et al. |
| 2008/0058816 A1 | 3/2008 | Philippon et al. |
| 2008/0097491 A1 | 4/2008 | Gobel |
| 2008/0109038 A1 | 5/2008 | Steiner et al. |
| 2008/0109080 A1 * | 5/2008 | Aeschlimann ..... A61B 17/8872 623/16.11 |
| 2008/0167660 A1 | 7/2008 | Moreau et al. |
| 2008/0208253 A1 | 8/2008 | Dreyfuss et al. |
| 2008/0269743 A1 | 10/2008 | McNamara et al. |
| 2009/0112270 A1 | 4/2009 | Lunn et al. |
| 2009/0131947 A1 | 5/2009 | Aeschlimann et al. |
| 2009/0138053 A1 | 5/2009 | Assell et al. |
| 2009/0171394 A1 | 7/2009 | Abdou |
| 2009/0187216 A1 | 7/2009 | Schmieding et al. |
| 2009/0192546 A1 | 7/2009 | Schmieding et al. |
| 2009/0204152 A1 | 8/2009 | Blain |
| 2009/0264928 A1 | 10/2009 | Blain |
| 2010/0016869 A1 | 1/2010 | Paulk et al. |
| 2010/0023057 A1 | 1/2010 | Aeschlimann et al. |
| 2010/0030263 A1 | 2/2010 | Cheng |
| 2010/0049179 A1 | 2/2010 | Kanaoka et al. |
| 2010/0069958 A1 | 3/2010 | Sullivan |
| 2010/0152773 A1 | 6/2010 | Lunn et al. |
| 2010/0179573 A1 | 7/2010 | Levinsohn et al. |
| 2010/0211120 A1 | 8/2010 | Bonutti et al. |
| 2010/0217266 A1 | 8/2010 | Helevirta et al. |
| 2010/0262186 A1 | 10/2010 | Sodeika et al. |
| 2010/0331881 A1 | 12/2010 | Hart |
| 2011/0046670 A1 | 2/2011 | Lehmann et al. |
| 2011/0071545 A1 | 3/2011 | Pamichev et al. |
| 2011/0118744 A1 | 5/2011 | Lehmann et al. |
| 2011/0276064 A1 | 11/2011 | Henrichsen et al. |
| 2011/0276091 A1 | 11/2011 | Melanson et al. |
| 2012/0053623 A1 | 3/2012 | Sojka et al. |
| 2012/0071877 A1 | 3/2012 | Frigg |
| 2012/0078278 A1 | 3/2012 | Sklar |
| 2012/0179200 A1 | 7/2012 | Cauldwell et al. |
| 2012/0191142 A1 | 7/2012 | Bouduban et al. |
| 2012/0203340 A1 | 8/2012 | Choinski et al. |
| 2012/0239085 A1 | 9/2012 | Schlotterback et al. |
| 2012/0245631 A1 | 9/2012 | Lunn et al. |
| 2012/0245634 A1 | 9/2012 | Kaplan |
| 2012/0330327 A1 | 12/2012 | McClellan |
| 2013/0006276 A1 | 1/2013 | Lantz et al. |
| 2013/0006302 A1 | 1/2013 | Paulk et al. |
| 2013/0023930 A1 | 1/2013 | Stone et al. |
| 2013/0035721 A1 | 2/2013 | Brunelle |
| 2013/0046340 A1 | 2/2013 | Huxel et al. |
| 2013/0072976 A1 | 3/2013 | Van Der Burg et al. |
| 2013/0079818 A1 | 3/2013 | Lizardi |
| 2013/0096611 A1 | 4/2013 | Sullivan |
| 2013/0103081 A1 | 4/2013 | Wolf |
| 2013/0123845 A1 | 5/2013 | Paulk et al. |
| 2013/0123848 A1 | 5/2013 | Duggal et al. |
| 2013/0138123 A1 | 5/2013 | Stone et al. |
| 2013/0138152 A1 | 5/2013 | Stone et al. |
| 2013/0144334 A1 | 6/2013 | Bouduban et al. |
| 2013/0144335 A1 | 6/2013 | Sandow |
| 2013/0144343 A1 | 6/2013 | Arnett et al. |
| 2013/0150885 A1 | 6/2013 | Dreyfuss |
| 2013/0158597 A1 | 6/2013 | Hernandez |
| 2013/0158598 A1 | 6/2013 | Lizardi |
| 2013/0158599 A1 | 6/2013 | Hester |
| 2013/0165972 A1 | 6/2013 | Sullivan |
| 2013/0178901 A1 | 7/2013 | Arai et al. |
| 2013/0184748 A1 | 7/2013 | Sojka et al. |

FOREIGN PATENT DOCUMENTS

| | | |
|---|---|---|
| JP | 4-250155 | 9/1992 |
| JP | 08-052154 | 2/1996 |
| JP | 2006-512144 | 4/2006 |
| JP | 2009-517156 | 4/2009 |
| JP | 2013-537818 | 10/2013 |
| WO | 2008/128367 | 10/2008 |
| WO | 2008/131884 | 11/2008 |
| WO | 2009/055952 | 5/2009 |
| WO | 2009/109057 | 9/2009 |
| WO | 2009/132472 | 11/2009 |
| WO | 2009/141252 | 11/2009 |
| WO | 2010/045751 | 4/2010 |
| WO | 2010/117982 | 10/2010 |
| WO | 2012/006161 | 1/2012 |
| WO | 2013/052690 | 4/2013 |

(56) References Cited

FOREIGN PATENT DOCUMENTS

OTHER PUBLICATIONS

Extended European Search Report dated Jan. 23, 2020, Application No. EP 19 21 4033, 9 pages.

* cited by examiner

SUTURE ANCHOR AND METHOD FOR FIXATING A SUTURE RELATIVE TO HARD TISSUE

FIELD OF THE INVENTION

The invention is in the field of medical technology and concerns a suture anchor and a method for fixating a suture relative to hard tissue, in particular with the aim of attaching soft tissue to the hard tissue with the aid of the suture, wherein the hard tissue is in particular bone tissue of a human or animal patient.

BACKGROUND OF THE INVENTION

The publications U.S. Pat. No. 7,008,226, WO 2009/109057 and WO 2009/055952 (all to Woodwelding) disclose devices and methods for attaching a suture to hard tissue with the aid of a suture anchor, wherein the suture anchor comprises a material having thermoplastic properties and is anchored in a hard tissue opening with the aid of preferably vibratory energy used for in situ liquefaction of the material having thermoplastic properties. The liquefied material penetrates into pores or other suitable structures of the hard tissue of the wall of the hard tissue opening, where on re-solidification it constitutes a positive fit connection between the hard tissue and the suture anchor. The anchor comprises the material having thermoplastic properties on a circumferential surface or in the form of a thermoplastic sleeve and it is liquefied when the anchor is forced into the hard tissue opening and simultaneously vibrated or when the anchor or part thereof is positioned in the hard tissue opening and the thermoplastic sleeve is held between a vibrating tool and a counter element. The suture is threaded through the proximal or distal end of the suture anchor.

Further suture anchors and methods for fixating sutures to hard tissue are disclosed in the publications U.S. Pat. Nos. 7,678,134, 7,695,495, US-2006/161159, US-2009/192546, US-2009/187216 (all to Arthrex), U.S. Pat. No. 5,733,307 (Dinsdale), or U.S. Pat. No. 6,508,830 (Steiner), wherein the disclosed anchors comprise an interference screw to be screwed into a bone opening provided for the purpose, or a plug preferably made of bone material to be press-fitted into a bone opening provided for the purpose, wherein the suture is either held by the screw or plug or by an additional element being retained in the opening with the aid of the screw or plug.

Methods of anchoring an item in an opening provided in hard tissue, e.g. in bone tissue of a human or animal patient with the aid of a material having thermoplastic properties which is liquefied in situ and made to penetrate the hard tissue of the wall of the opening are furthermore disclosed in the publications U.S. Pat. No. 7,335,205, US-2006/0105295, US-2008/109080, US-2009/131947, WO-2009/109057, and WO-2009/132472. Therein preferred energy used for the liquefaction is mechanical vibration energy. The disclosure of all the named publications and applications is enclosed herein by reference.

SUMMARY OF THE INVENTION

It is the object of the invention to create a further suture anchor and a further method for fixating a suture relative to hard tissue, wherein the suture anchor is fixated in a hard tissue opening with the aid of a material having thermoplastic properties which is liquefied in situ to penetrate the hard tissue of the wall of the hard tissue opening. Therein the suture anchor and the method are to be suitable for attaching soft tissue to the hard tissue with the aid of the suture, and the hard tissue is to be in particular bone tissue of a human or animal patient. The suture is preferably fixated relative to the suture anchor or the hard tissue respectively in a non-slideable manner (suture locking), wherein suture tension may be adjustable during at least an initial section of the fixation process. However, the suture anchor according to the invention may also serve for establishing a slideable suture fixation. The method including suture locking is in particular suitable for per se known knot-less procedures for suturing soft tissue to hard tissue. Furthermore, the suture anchor and method according to the invention are to be capable of safeguarding the suture against undesired influence caused by the in-situ liquefaction (i.e., in the case of liquefaction through mechanical vibration, against undesired influences of friction and heat), and to therefore allow use in connection with friction and/or heat sensitive sutures. Furthermore, a distal end of the anchor may be equipped for enhancing retainment of the suture anchor in the hard tissue opening, in particular in hard tissue with only little mechanical stability.

The suture anchor according to the invention comprises a material having thermoplastic properties at least on surface portions to be in contact with the hard tissue in the hard tissue opening or preferably it consists fully of such a material, wherein at least part of the material having thermoplastic properties is liquefied in situ and penetrates the hard tissue of the walls of the opening. The distal suture end comprises a suture conduit for holding the suture, e.g. a distal suture groove, a suture channel or an eyelet, of more than one such conduit or a combination of different ones of such conduits. The suture anchor is designed, in particular, for locking the suture relative to the anchor in a last phase of the process of fixating the anchor in the hard tissue, wherein the locking of the suture is achieved either by clamping the suture between the anchor and the hard tissue in the hard tissue opening or by braking or clamping it through collapse of the suture conduit or suture conduits. This means that the locking of the suture does principally not depend on the fixation process in which the suture anchor is fixated or anchored in the hard tissue opening, which allows safeguarding the suture against possibly damaging influences of the liquefaction process (heat, vibration) and/or allows adjustment of the suture tension during or possibly even after the anchoring process.

Furthermore, the suture anchor may comprise structures preferably in a distal end portion which structures are capable of being spread or radially expanded by suture tension and/or abutment of the distal anchor end against the bottom of a blind opening, which spreading or expanding enhances retainment in or beyond the hard tissue opening. The named spreading is e.g. effected during the liquefaction process by the tensioned suture being forced against or into the anchor material proximal to the suture conduit when this anchor material is mechanically weakened by absorption of heat, which may result in distal anchor sections being forced apart, such spreading the distal anchor portion. In a further embodiment a portion of the anchor is designed to be collapsible under a compressive load and can therewith be radially expanded e.g. under the influence of the suture tension.

For the fixation process, for which mechanical vibration energy (in particular ultrasonic vibrational energy) is preferably used, the suture anchor according to the invention is forced into the hard tissue opening and simultaneously the liquefaction energy is transmitted into the material to be liquefied. For this purpose, a tool suitable for transmitting a pushing force and the vibrational energy to the anchor is used, a distal end of the tool being preferably attached to the proximal face of the suture anchor and a proximal end of the tool being coupled to a vibration source. This fixation process does not necessitate any rotation of the suture anchor, i.e. the suture anchor is not screwed into the hard tissue opening and therefore preferably does not comprise a screw thread.

The vibration source is in particular a source of ultrasonic vibration (e.g. piezoelectric vibration generator possibly comprising a booster to which the tool is coupled) and the tool is suitable for transmission of the vibration from its proximal end to its distal face, preferably such that the distal face vibrates with a maximal longitudinal amplitude. For the in situ liquefaction, the distal face of the tool is applied to the proximal face of the suture anchor. It is possible also to activate the tool to vibrate in a radial or in a rotational direction.

Alternatively, the energy source may be a laser, preferably emitting laser light in the visible or infrared frequency range and the tool is equipped for transmitting this light to its distal end, preferably via glass fiber. For the in situ liquefaction, the laser light is absorbed near the distal tool face or in the suture anchor, wherein in the latter case the material having thermoplastic properties comprised by the suture anchor may contain particles or substances effecting such absorption. Furthermore, the energy source may be a source of electric energy which e.g. heats an electric resistor in a distal tool portion or which causes eddy currents and therewith thermal energy near the distal tool face or in the suture anchor.

Suitable in situ liquefaction of a material having thermoplastic properties with the aid of vibration energy combined with an acceptable thermal loading of the tissue and suitable mechanical properties of the positive fit connection to be produced is achievable by using materials with thermoplastic properties having an initial modulus of elasticity of at least 0.5 GPa and a melting temperature of up to about 350° C. in combination with vibration frequencies preferably in the range of between 2 and 200 kHz (preferably 15 to 40 kHz, or even more preferably between 20 and 30 kHz). The modulus of elasticity of at least 0.5 GPa is in particular necessary if the material having thermoplastic properties is to transmit the vibration without loss of mechanical stiffness.

Materials having thermoplastic properties suitable for the suture anchor according to the invention are thermoplastic polymers, e.g.: resorbable or degradable polymers such as polymers based on lactic and/or glycolic acid (PLA, PLLA, PGA, PLGA etc.) or polyhydroxy alkanoates (PHA), poly-caprolactone (PCL), polysaccharides, polydioxanes (PD) polyanhydrides, polypeptides or corresponding copolymers or composite materials containing the named polymers as a component; or non-resorbable or non-degradable polymers such as polyolefines (e.g. polyethylene), polyacrylates, polymetacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylensulfides, polysulfones, polyethers or equivalent copolymers or composite materials containing the named polymers as a component.

Specific embodiments of degradable materials are Polylactides like LR706 PLDLLA 70/30 (e.g. filled with up to 30% biphasic calciumphosphate), R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Specific embodiments of non-degradable materials are Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonate-urethane (e.g. Bionate by DSM, in particular types 65D and 75D). An overview table of polymers and applications is listed in Wintermantel, page 150; specific examples can be found in Wintermantel page 161 ff. (PE, Hostalen Gur 812, Höchst AG), pages 164 ff. (PET), 169ff. (PA, namely PA 6 and PA 66), 171 ff. (PTFE), 173 ff. (PMMA), 180 (PUR, see table), 186 ff. (PEEK), 189 ff. (PSU), 191 ff (POM—Polyacetal, tradenames Delrin, Tenac, has also been used in endoprostheses by Protec).

The material having thermoplastic properties may further contain foreign phases or compounds serving further functions. In particular, the thermoplastic material may be strengthened by admixed fibers or whiskers (e.g. of calcium phosphate ceramics or glasses) and such represent a composite material. The material having thermoplastic properties may further contain components which expand or dissolve (create pores) in situ (e.g. polyesters, polysaccharides, hydrogels, sodium phosphates), compounds which render the implant opaque and therewith visible for X-ray, or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed. If the device is to be anchored not with the aid of vibration energy but with the aid of electromagnetic radiation, the liquefiable material having thermoplastic properties may locally contain compounds (particulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalcium phosphate (TCP), Hydroxyapatite (HA, <90% crystallinity); or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can, for example, be found in X. Huang and X. Miao, J Biomater App. 2007 April; 21(4):351-74), J A Juhasz et al. Biomaterials, 2004 March; 25(6):949-55. Particulate filler types include: coarse type: 5-20 μm (contents, preferentially 10-25% by volume), submicron (nanofillers as from precipitation, preferentially plate like aspect ratio >10, 10-50 nm, contents 0.5 to 5% by volume). Experiments show that liquefaction with the aid of ultrasonic vibration energy allows filling the thermoplastic polymer to a relatively high degree without impairing the capability of the liquefied material to penetrate structures as e.g. the trabecular structure of viable cancellous bone.

The suture anchor according to the invention may, in addition to the material having thermoplastic properties, also comprise portions (e.g. a core) of material having no thermoplastic properties or thermoplastic properties which are not suitable for in situ liquefaction under the conditions of the fixating process (non-liquefiable materials). Such portions may consist of any suitable material (e.g. polymer, metal, ceramic, glass) which may be bio-resorbable or not bio-resorbable. Such non-bioresorbable or non-biodegradable portions may comprise surfaces equipped for furthering osseointegration (e.g. per se known surface structures or coatings) where in contact with the bone tissue, in particular if the material having thermoplastic properties is bio-resorbable or bio-degradable and therefore the anchoring function needs to be gradually taken over by osseointegration. Suitable non-liquefiable materials, which are bio-resorbable, are e.g. polylactic acid (PLA) filled with Hydroxyapatite or calciumphosphates, in particular PLLA filled with 60% tricalciumphosphate.

The vibration tool can be designed very slim and approximately 200 mm long or even longer. Therefore, the suture anchor and method according to the invention are in particular suitable for minimally invasive surgery but are also applicable in open surgery. The vibration tool preferably has a length corresponding to half of the vibration wavelength in the tool material or of this half wavelength multiplied with an integer factor, the theoretical half wavelength e.g. for a tool made of titanium grade 5 and for a vibration frequency of 20 kHz being 126.5 mm, for a vibration frequency of 25 kHz 101.2 mm.

The device and method according to the invention as above described are in particular applicable for substantially all surgical procedures in a human or animal patient, in which surgical procedure a suture needs to be attached to hard tissue and locked relative to the latter, some of the embodiments being in particular advantageous in hard tissue of only little mechanical strength. In the same manner, the suture anchor and the method according to the invention are applicable for attaching a suture to a replacement material having features comparable to the features of hard tissue, or to part hard tissue part replacement material or to a further implant (e.g. endoprosthesis) wherein the implant needs to be suitably equipped, e.g. with undercut openings.

Figure 1:
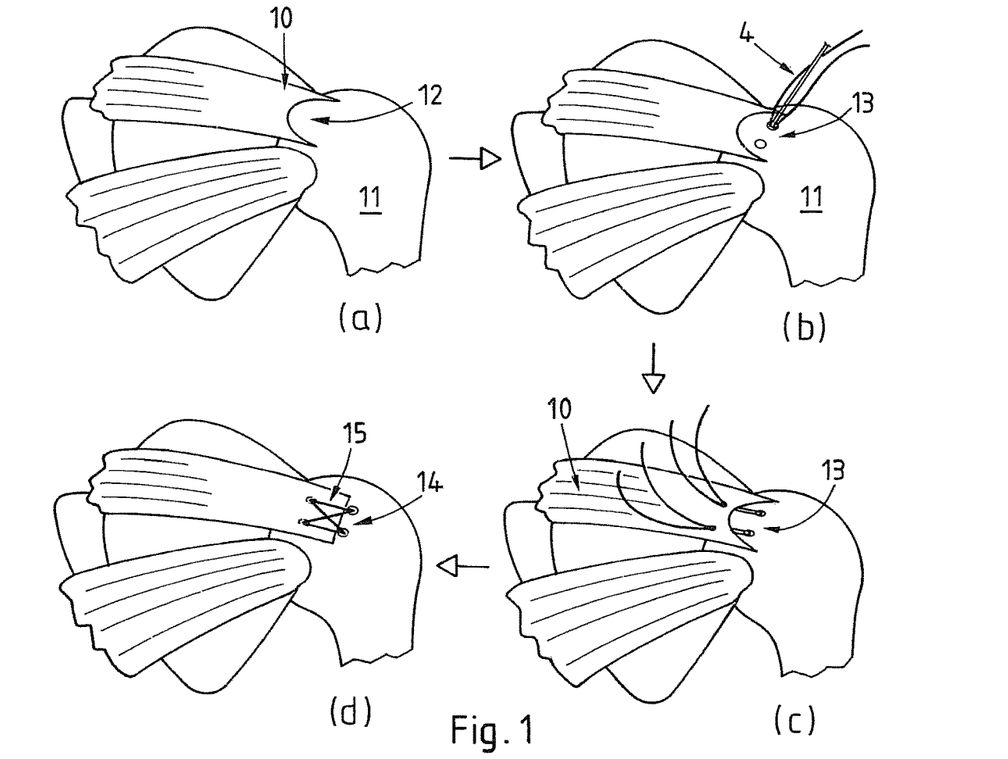
FIG. 1 illustrates four successive phases of the per se known double row procedure using the example of a rotator cuff repair, in which procedure the anchor according to the invention preferably constitutes the anchors of the lateral row but possibly also the anchors of the medial row.

Examples of such applications are the fixation of a soft tissue (in particular ligament, tendon or cartilaginous tissue) to bone tissue in a so called knot-less single row procedure, e.g. fixation of a rotator cuff to underlying bone tissue (or a corresponding endoprosthesis), Achilles tendon repair, reattachment of the acetabular labrum to the acetabulum or the glenoid labrum to the scapula or, as lateral anchors in a so called double row procedure (see FIG. 1). In the latter case it is advantageous to use the same fixation process for fixation of the anchors (without the suture locking) of the medial row also. Preferred devices and methods for fixating such medial anchors are e.g. disclosed in a co-pending application claiming the same priority. However, the suture anchor and the method according to the invention may also be used for slideable attachment of a suture to hard tissue (e.g. for the medial anchors in a double row procedure).

Further exemplary applications of the anchor and method according to the invention are e.g. regarding the human shoulder joint: the Bankart repair or the repair of SLAP-lesions (superior labrum anterior to posterior), regarding the human hand: the UCL-repair (ulnar collateral ligament) as treatment for "skier's thumb" (acute condition) or "gamekeeper's thumb" (chronic condition), the SL-reconstruction (scapholunate ligament), the TFCC-repair (triangular fibrocartilagecomplex), or the capsular reattachment of the metacarpophalangeal joint, regarding the human elbow: ulnar collateral ligament reconstruction (Tommy John surgery), regarding the human foot: the Bromström repair, the peroneal retinacular repair or halux valgus reconstruction, and regarding the human knee: iliotibial band tenodesis. Generally speaking, the suture anchor and method according to the invention are particularly advantageously applicable in repair surgery regarding ligaments in the human hand and wrist (ligaments of interphalangeal, metaphalangeal and carpometaphalangeal joints and carpal ligaments) and in the human foot and ankle joint.

BRIEF DESCRIPTION OF THE DRAWINGS

The suture anchor and the method according to the invention are described in further detail in connection with the appended Figs., wherein.

DESCRIPTION OF THE PREFERRED EMBODIMENTS

FIG. 1 illustrates the per se known double row procedure for suturing a soft tissue to a hard tissue, using the example of reattaching a torn rotator cuff tendon 10 to humeral bone tissue 11 (or a corresponding endoprosthesis) in four successive phases (a), (b), (c) and (d). Phase (a) is before the repair operation and shows the location 12 in which reattachment is necessary. In phase (b) two medial anchors 13 are anchored in the bone tissue, in locations to eventually be located underneath the tendon 10, each one of the medial anchors 13 attaching at least one suture 4 to the bone tissue in a slideable manner. In phase (c) the end sections of each suture attached to one of the medial anchors is passed through the torn tendon 10 and by tensioning the sutures away from the tendon end (not shown), the latter is pulled over the medial anchors 13. In phase (d) two lateral anchors 14 are anchored in the bone tissue just beyond the edge of the tear, the row of lateral anchors 14 running about parallel to the row of medial anchors 13, the end sections of the sutures 4 being tensioned and locked with the aid of the lateral anchors 14 in a cross-wise manner, such that the two suture end sections held by one medial anchor 13 are locked by two different lateral anchors 14 such forming crossed suture bridges 15 between the row of medial anchors 13 and the row of lateral anchors 14. Therein each row of anchors may comprise two or more than two anchors and each medial anchor 13 is used for attaching at least one suture 4 (two suture end portions) and each lateral anchor 14 is used for locking at least two suture end portions originating from two different medial anchors 13.

As already mentioned further above, the suture anchor and the method according to the invention are in particular advantageously applicable in the lateral row, but correspondingly adapted are also applicable in the medial row.

Figure 2:
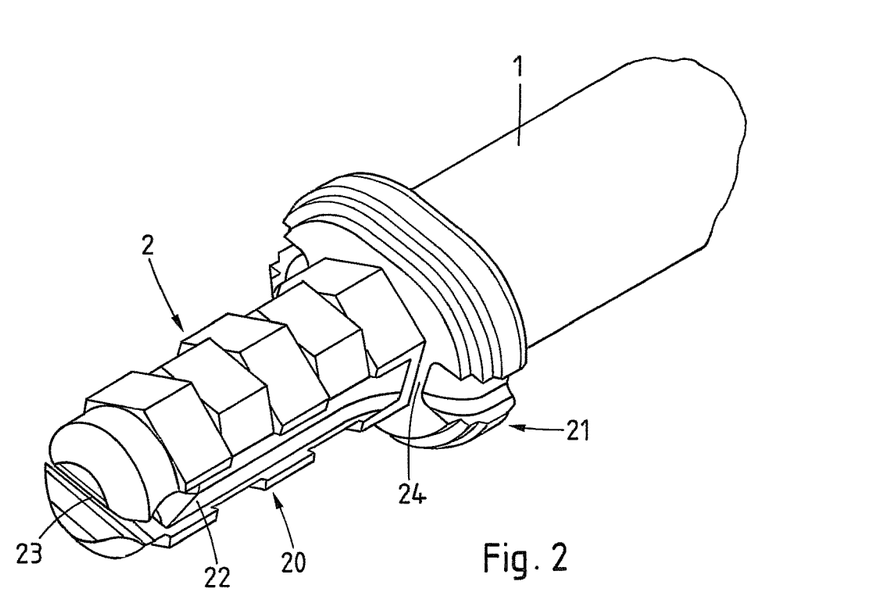
FIG. 2 shows an exemplary embodiment of the suture anchor according to the invention, the suture anchor being suitable for locking the suture between the hard tissue and the suture anchor.
Figure 3:
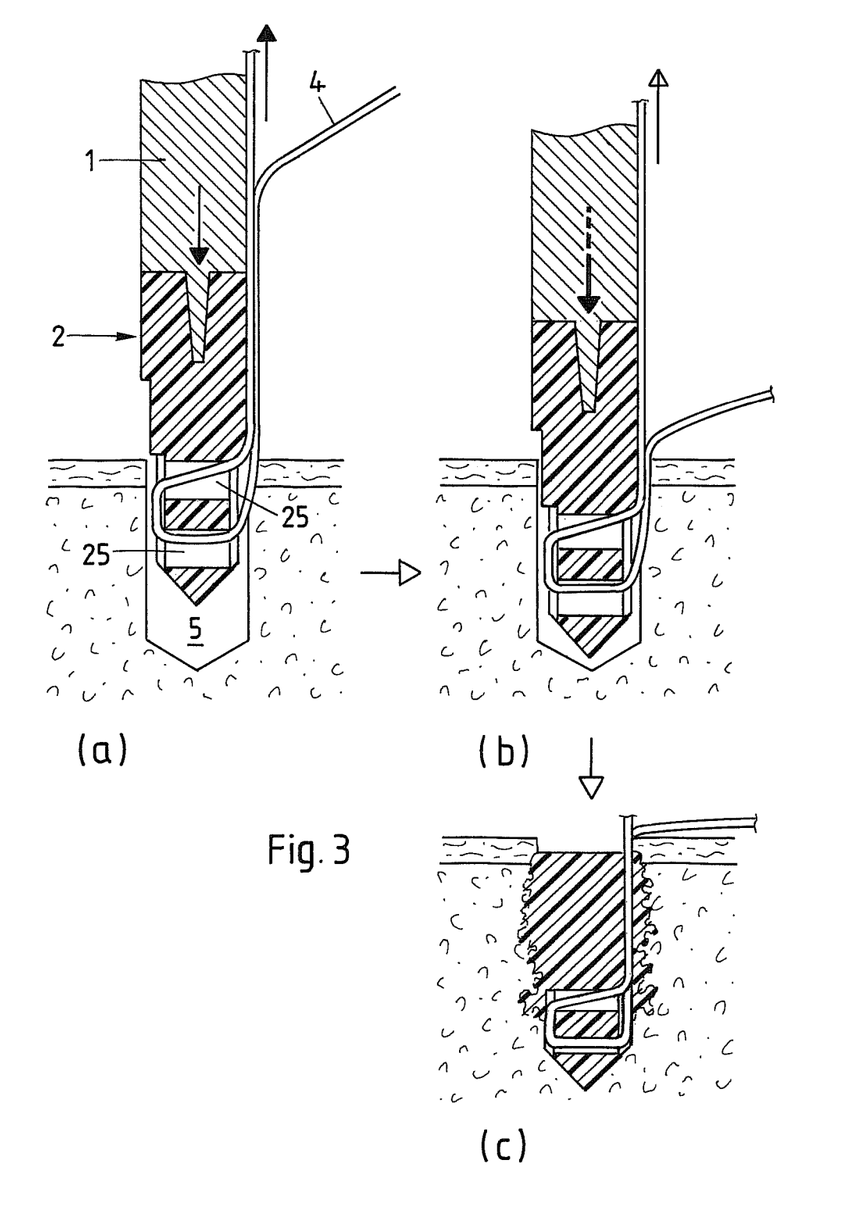
FIG. 3 shows a further exemplary embodiment of the suture anchor according to the invention, the suture anchor being suitable for locking the suture by collapsing the suture conduit.

FIGS. 2 and 3 illustrate exemplary embodiments of the suture anchor according to the invention. These suture anchors 2 comprise a material having thermoplastic properties (liquefiable material) or they are preferably made of such a material and they are anchored in a hard tissue opening by in situ liquefaction of at least part of the material having thermoplastic properties and by making the liquefied material flow into the hard tissue to constitute, when re-solidified, a positive fit connection between the anchor and the hard tissue. The anchoring method on which the anchors, according to the invention, are based is disclosed e.g. in the publication U.S. Pat. No. 7,335,205, the disclosure of which is enclosed herein in its entirety. According to this method a proximal face of the anchor is contacted with a tool which transmits energy into the anchor, in particular a vibration tool which transmits vibrational energy. Simultaneously the anchor is pushed into a hard tissue opening having a cross section which is slightly smaller than the cross section of the anchor portion to be fixated in the opening, such that anchor portions comprising the material having thermoplastic properties get into intimate contact with the hard tissue, which in the case of the use of vibrational energy serves also as counter element necessary for transforming the vibrational energy into friction heat for the in situ liquefaction.

Furthermore, the suture anchors according to FIGS. 2 and 3 comprise at least one distal suture conduit (e.g. distal groove, channel, or eyelet) in which the suture is held when the suture anchor is positioned relative to the hard tissue opening and fixated therein, and structures for locking the suture relative to the fixated anchor or the hard tissue respectively either by clamping it between the suture anchor and the wall of the hard tissue opening (FIG. 2) or by collapsing the suture conduit and such braking or clamping the suture threaded therethrough (FIG. 3).

The suture anchor 2 as shown in FIG. 2 comprises a pin portion 20 and advantageously a head portion 21 and is shown attached to a tool 1, by e.g. a press fit connection between a tool protrusion reaching into a recess in the head portion 21 (not shown). At least the pin portion 20 comprises at least at parts of its lateral surfaces the material having thermoplastic properties and advantageously, as illustrated, energy directors e.g. in the form of axial edges extending over part of the pin length and being offset relative to each other in adjoining such part lengths (the pin portion has e.g. as illustrated the form of a stack of misaligned polygon-shaped discs). The head portion 21 may also comprise the material having thermoplastic properties and may also be anchored in the hard tissue, in which case the hard tissue opening provided for the anchor 2 will need to have a stepped form including a narrower inner portion for accommodation of the pin portion 20 and a larger outer portion for accommodation of the head portion 21. Alternatively, the distal face of the head portion my be anchored in the hard tissue surface around the mouth of the opening provided for the pin portion.

The pin portion 20 comprises a suture groove 22 running across the distal pin face and, in an axial direction, along two opposite pin sides, wherein the suture groove 22 comprises at least one portion which is undercut, the undercut groove portion 23 being situated e.g. as illustrated, on the distal pin face (suture conduit). Preferably, the overall cross section of the suture groove 22 is adapted to the suture or sutures to be locked with the aid of the anchor such that the suture(s) running along the groove does not protrude from the groove, i.e. does not get into contact with the hard tissue when the pin portion 20 is pushed into the hard tissue opening provided therefore while being vibrated. This measure serves for preventing damage of a friction and/or heat sensitive suture on fixation of the anchor, in particular when using vibrational energy for such fixation. When using a suture of no such sensitivity the suture may as well protrude from the suture groove and therewith rub on the wall of the hard tissue opening, wherein such friction may help to at least primary stabilization of the suture relative to the suture anchor.

The undercut portion 23 of the suture groove 22 is dimensioned such that the suture to be locked with the aid of the anchor can be entered into the undercut groove by resiliently deforming the groove entrance and that the suture is safely kept in the undercut groove portion 23 when no force acting perpendicular to the groove length pulls the suture out of the undercut groove portion 23.

The suture groove 22 continues on both sides of the head portion 21, but at the transition between pin and head portion comprises an interruption 24, i.e. it has a depth on a proximal end of the pin portion 20 which decreases with decreasing distance form the head portion 21, a zero-depth portion (or portion with relevantly reduced depth) at the transition between the pin and the head portion, and a depth on a distal side of the head portion 21 which increases with increasing distance from the pin portion 20. This measure serves for clamping the suture between the hard tissue and the implanted anchor for locking it.

The head portion 21 has a larger cross section than the distal end of the tool 1 such that, when the anchor 2 is attached to this distal tool end, the proximal face of the head protrudes beyond the distal face of the tool at least on those two sides on which the suture groove reaches this proximal head face. As illustrated, the distal tool end may have a circular cross section and the head portion an oval cross section having a smaller diameter which is the same as the tool diameter and a larger diameter spanning between the mouths of the suture grooves. This measure serves for preventing a friction and/or heat sensitive suture from contact with the tool 1, in particular with the edge of the distal tool face, which is particularly advantageous when the tool is a vibration tool and the suture is of a friction and/or heat sensitive type.

For fixating a suture relative to hard tissue using the anchor 2 as illustrated in FIG. 2, a hard tissue opening is provided, a cross section of at least an inner portion of the hard tissue opening being adapted to the pin portion 20 of the anchor 2 such that a distal end of the pin portion 20 having the smallest cross section fits easily into the opening but the rest of the pin portion 20 can be introduced into the opening using a pressing force only. The pin portion 20 of the anchor which is attached to the tool being coupled to an energy source (preferably vibration source) is positioned into the mouth of the opening, the suture to be fixated by the anchor running along the suture groove 22 and extending out of the hard tissue opening on both sides of the anchor. The pressing force is then applied to the suture anchor via the tool, the desired suture tension is established and the energy source is activated (tool and anchor vibrated). Where in intimate contact with the hard tissue wall of the opening, the material having thermoplastic properties is liquefied and penetrates into the hard tissue. At the same time the anchor is pushed further into the opening and is finally anchored when the head portion 21 abuts the hard tissue surface or a step in the hard tissue opening. Only at the very end of the described anchoring process, the suture is clamped between the hard tissue in the region of the mouth of the hard tissue opening or the step in the opening and the suture anchor at the transition from the pin portion 20 to the head portion 21, which transition location only then reaches the hard tissue. This means that the suture, if correspondingly adapted to the suture groove, remains slideable (possibly against some friction between suture and tissue inside the hard tissue opening) relative to the anchor during an initial part of the fixation step and therefore the suture tension can still be adapted or maintained up to when the anchor is very close to its final fixated position.

Further embodiments of the suture anchor as illustrated in FIG. 2 may e.g. not comprise a head portion, comprise energy directors of a different type or no energy directors at all and/or may comprise a core not being made of the material having thermoplastic properties but comprising a sleeve of or being coated with the latter at least on the pin portion and possibly excepting the suture groove 22 and the distal pin end.

When used for locking sutures which are neither friction nor heat sensitive, and without the possibility of the late tension adjustment, the suture groove may be present at the distal face of the pin section 20 only (zero depth suture groove portion extending along the entire anchor length), where it may be undercut or may have a cross section dimensioned for holding the suture by friction. The same effect can be achieved with a suture anchor as shown in FIG. 2 and a suture having a cross section greater than the cross section of the suture groove 22 (possibly not having a zero depth portion at all), wherein the suture protrudes from the groove. For achieving a slideable attachment of the suture to the hard tissue using the suture anchor according to FIG. 2 or a similar suture anchor, a suture of a diameter smaller than the reduced depth of the zero-depth groove portion is used, or the anchor is introduced into the hard tissue opening only such that the zero-depth groove portion protrudes from the opening or the opening is provided with a mouth of a larger cross section to accommodate the zero-depth groove portion without clamping the suture.

Furthermore, the head portion 21 may comprise a protrusion suitable for attachment of the anchor 2 to the tool 1 which has a corresponding recess in its distal face. Furthermore, the suture anchor according to FIG. 2, in particular the embodiment comprising a core of e.g. a metal may comprise a tapering or sharpened distal end for being able to be forced at least into cancellous bone without the necessity of providing an opening therein beforehand or of providing such opening only through the cortical bone. The forcing of the suture anchor 2 into the bone tissue is preferably effected using the same tool as used for the anchoring step but without transmitting energy for the liquefaction to the suture anchor.

The anchor as illustrated in FIG. 3 differs form the anchor as illustrated in FIG. 2 mainly regarding the means provided for the suture locking, which in this case are located at the distal anchor end being equipped for holding the suture. This distal end has a smaller cross section than the rest of the anchor and comprises two eyelets 25 (suture conduit) and it consists of a material which is plastically deformable or becomes plastically deformable under the influence of energy transmitted into the anchor for its fixation in the hard tissue such that a compressive load, caused through the suture tension and/or by abutment against a bottom wall of a blind hard tissue opening is able to collapse it (collapsible suture conduit). The suture 4 to be fixated and locked with the aid of the anchor 2 is threaded through the two eyelets 75 and runs along the anchor length e.g. in a suture groove as described further above in connection with FIG. 2, but not shown in FIG. 3.

The anchor 2 as illustrated in FIG. 3 is fixated in a hard tissue opening 5 much as discussed above in connection with FIG. 2, wherein the distal pin end comprising the two eyelets 25 is made to collapse by the suture being tensioned against the anchor and/or by pushing it against the hard tissue on the bottom of the opening 5 provided for the anchor 2, wherein by such collapse the suture 4 is locked due to its bending radius between the two eyelets 25 being reduced and therewith suture braking increased in such a manner that the suture cannot slide therethrough any more and/or due to the decreasing cross section of the eyelets 25 which causes the suture 4 to be clamped. In such a case the zero-depth portion of the suture groove as described above is not needed for securely locking the suture, which means that in this latter case, there may be no contact at all between the suture 4 and the hard tissue within the opening 5.

FIG. 3 shows, in a very schematic manner, the anchor 2 in three successive phases (a), (b) and (c) during the fixation and locking process. In phase (a) the anchor 2 being attached to the distal end of the tool 1 is positioned in the mouth of the hard tissue opening 5, the suture 4 running through the two eyelets 25 and out of the opening 5 at one side of the anchor 2 to be held by any suitable means. In phase (b) the tool 1 is activated by the not shown energy source and the anchor 2 is pushed further into the opening 5, while the suture 4 is kept tensioned or the suture tension is increased, possibly against friction between the suture and the tissue in the hard tissue opening. In phase (c), fixation of the anchor 2 and locking of the suture 4 are complete, the distal end of the anchor 2 abutting the bottom of the hard tissue opening 5 and comprising the two eyelets 25 being collapsed to brake and/or clamp the suture. The moment during the anchoring process in which the suture conduit is collapsed is determined by the suture tension which for this purpose needs to be sufficiently high and/or by the depth of the hard tissue opening 5. Up to the moment of the collapse of the eyelets 25, the suture 4 may remain slideable relative to the anchor, the same as discussed above in connection with FIG. 2.

For providing a slideable suture attachment using the suture anchor according to FIG. 3, the suture tension is to be kept sufficiently low and/or the hard tissue opening needs to be sufficiently deep.

The features listed above for further embodiments of the suture anchor according to FIG. 2 are, correspondingly adapted, also applicable for the suture anchor according to FIG. 3. Furthermore, features of the suture anchors according to FIGS. 2 and 3 can also be combined which results in further embodiments such as e.g. the suture anchor of FIG. 2 comprising a distal channel or eyelet for holding the suture, or comprising any distal suture conduit being collapsible, or the suture anchor of FIG. 3 comprising a collapsible distal groove which may be undercut, or comprising axial suture grooves with or without a proximal zero-depth portion.

Figure 4:
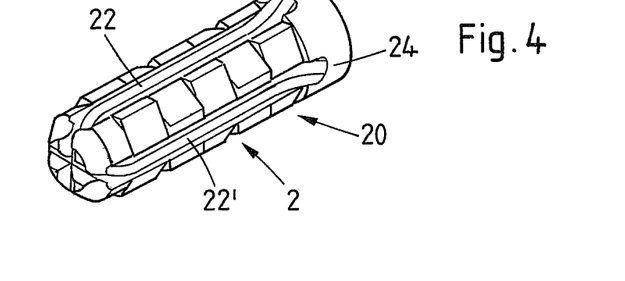
FIGS. 4 to 6 show further and alternative features applicable for the suture anchors shown in FIGS. 2 and 3.
Figure 5:
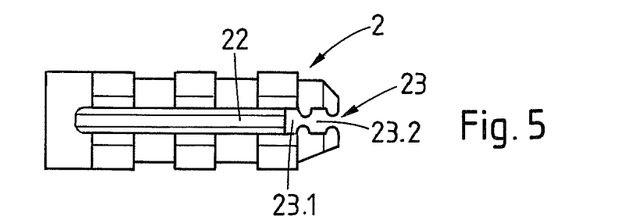
Figure 6:
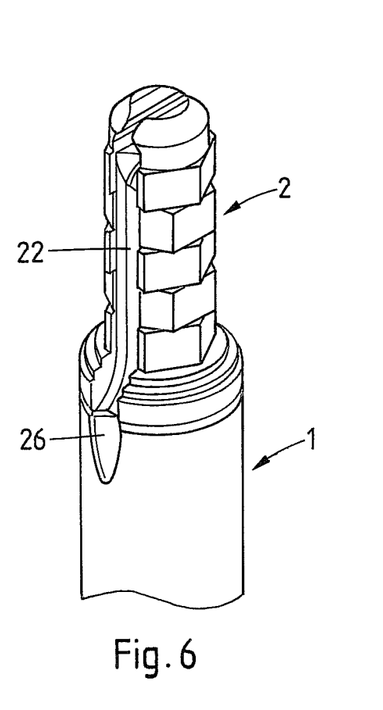

FIGS. 4 to 6 illustrate further exemplary embodiments of the suture anchor and method according to the invention, wherein some of these embodiments are mentioned already above as possible variations of the suture anchors according to FIGS. 2 and 3.

FIG. 4 shows a suture anchor 2 which is quite similar to the anchor as shown in FIG. 2 but other than the latter comprises a pin portion 20 only (no head portion) and instead of one suture groove for accommodation of one suture comprises two (or possibly more than two) suture grooves 22 and 22' for accommodation of two (or possibly more than two) sutures, wherein the two suture grooves extend cross-wise across the distal anchor face (suture conduits), where they are possibly undercut, and continue in an axial direction along the circumferential pin portion surface, preferably as illustrated regularly spaced from each other and ending at a distance from the proximal anchor face (zero-depth groove portions 24).

In the same manner as illustrated in FIG. 4, the suture anchor according to FIG. 3 may be equipped for anchoring more than one suture by comprising two or more than two distal suture conduits (eyelets) arranged at an angle to each other and possibly axial suture groves extending in a proximal direction from the mouths of the conduits.

FIG. 5 shows a suture anchor 2 similar to the suture anchors according to FIGS. 2 and 4 but comprising a suture groove 22 with an undercut distal groove portion 23 (suture conduit) constituting two groove levels, wherein the groove 23.1 of the inner level comprises a smaller cross section and in particular a narrower mouth than the groove 23.2 of the outer level, such that a thinner suture will enter the inner groove 23.1 and be safely held therein and a thicker suture possibly not being able to enter the inner groove 23.1 will be safely held in the outer groove 23.2. The suture anchor according to FIG. 5 is e.g. capable of resiliently holding sutures of a thread size from 0 to 3-0, wherein a thicker suture (e.g. size 0) will be held in the outer groove 23.2 and a thinner suture (e.g. 3-0) in the inner groove 23.1. This means that the anchor according to FIG. 5 is the same applicable for quite different thread sizes.

FIG. 6 illustrates a further means for safeguarding the suture to be fixated and possibly locked in hard tissue with the aid of the suture anchor according to the invention against possibly damaging influences caused by vibration or heat produced in the anchoring process. These further means are an equivalent to the head portion having a larger cross section than the tool used for implanting the anchor as shown in FIG. 2. Other than according to FIG. 2, in the present case, the safeguarding means are arranged on the tool 1 which is used for fixating the suture anchor in the hard tissue opening and which comprises at least on a distal end portion lateral grooves 26 which are arranged to be aligned with the proximal ends of the suture groove 22 of the suture anchor 2. The same as the protruding anchor head portions illustrated in FIG. 2, these lateral grooves 26 of the tool 1 prevent the suture from coming into contact with the edge of the distal face of the tool, which is in particular important for a vibration tool and for a suture which is friction and/or heat sensitive. If a zero-depth groove portion adjoins the proximal anchor face as illustrated in FIGS. 4 and 5 and the tool comprises a distal face adapted to the proximal anchor face or being slightly smaller, such measure does not have any advantage.

Figure 7:
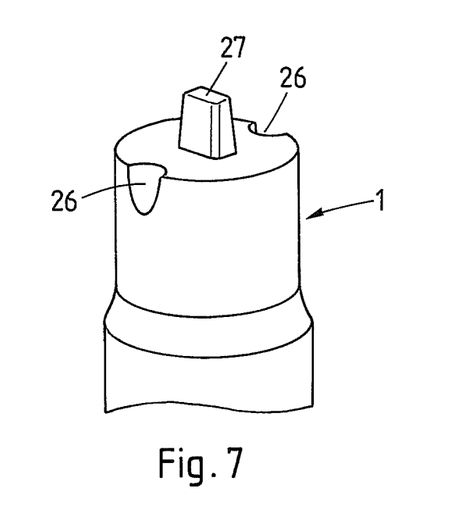
FIG. 7 shows in detail the distal end of an exemplary vibration tool suitable for fixation of the suture anchor according to FIG. 6.

FIG. 7 shows a distal face of a tool 1 comprising the lateral grooves 26 as discussed above and further comprising a protrusion 27 having an elongate, e.g. rectangular or oval cross section. In cooperating with a correspondingly shaped depression in the proximal anchor face attachment of the suture anchor to the distal tool end automatically results in proper alignment of the suture grooves 22 and the lateral grooves 26. Instead of a protrusion of an elongate cross section on the distal tool face and a corresponding depression in the proximal anchor face, two protrusions of an e.g. circular cross section and two corresponding bores in the proximal anchor face can be provided. The same is achieved obviously by the protrusion(s) being provided on the proximal anchor face and the depression(s) on the distal tool face.

FIGS. 8 to 11 illustrate distal ends of exemplary embodiments of the suture anchor according to the invention which embodiments constitute alternatives to distal anchor ends as shown in FIGS. 2 to 6. The suture anchor embodiments according to FIGS. 8 to 11 comprise in the same manner as the suture anchor embodiments according to FIGS. 2 to 6 a distal suture conduit (groove, channel or eyelet) extending angled relative to an anchor axis across a distal anchor face or through a distal anchor end portion. The anchor comprising a material having thermoplastic properties at least in the region of its circumferential surface is fixated in a hard tissue opening by having a cross section which is slightly larger than the cross section of the hard tissue opening and by being forced into the hard tissue opening and simultaneously being vibrated preferably by applying to a proximal anchor face a vibration tool being coupled e.g. to an ultrasonic vibration generator. The material having thermoplastic properties is liquefied at the interface between the vibrating suture anchor and the hard tissue of the wall of the opening provided for the suture anchor and penetrates this hard tissue to form on re-solidification a positive fit connection between the suture anchor and the hard tissue.

Using the suture anchors according to FIGS. 8 to 11, the fixation or anchorage established with the aid of the material having thermoplastic properties and the vibration energy (similar to the fixation or anchorage as discussed in connection with the previous figures), is enhanced by forcing apart distal anchor sections or expanding anchor portions, the forcing apart and the expansion being caused by the suture which during the fixation process is tensioned against the pushing force of the vibration tool and is therewith forced into or against the anchor portion proximal to the suture conduit and/or by the distal suture end being pushed against the bottom of a blind hard tissue opening into which the anchor is forced. Preferably this effect is further enhanced by providing for this anchor portion a material which is softened and thereby weakened on application of the liquefaction energy and/or by designing this anchor portion mechanically weaker than other anchor portions. Such spreading or expansion will enhance the retainment of the suture anchor constituted by the material having thermoplastic properties penetrated into the hard tissue of the wall of the opening, which is particularly advantageous if this hard tissue is e.g. cancellous bone tissue of only little mechanical strength positioned underneath a cortical bone layer. It is possible also that the spread anchor sections or the expanded anchor portion are situated beyond the hard tissue opening (on a non accessible side of a bone plate or cortical bone layer) and by having a larger cross section than the opening help retaining the anchor in the opening. It is obvious that in the latter case spreading and expansion can only be achieved through the suture tension.

Figure 8:
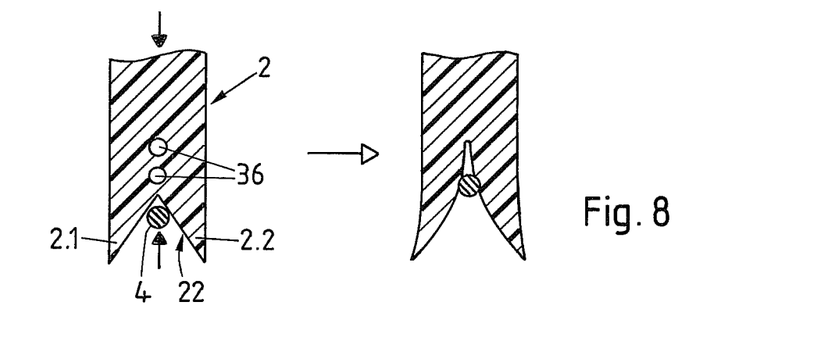
FIGS. 8 to 12 show further exemplary embodiments of distal ends for suture anchors according to the invention which are e.g. suitable for fixation in hard tissue of only little mechanical stability.
Figure 9:
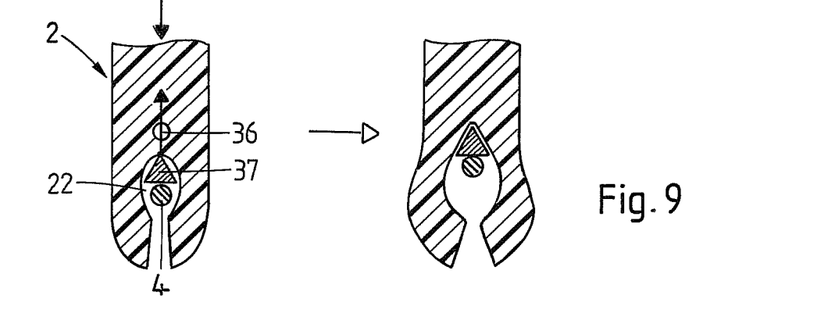
Figure 10:
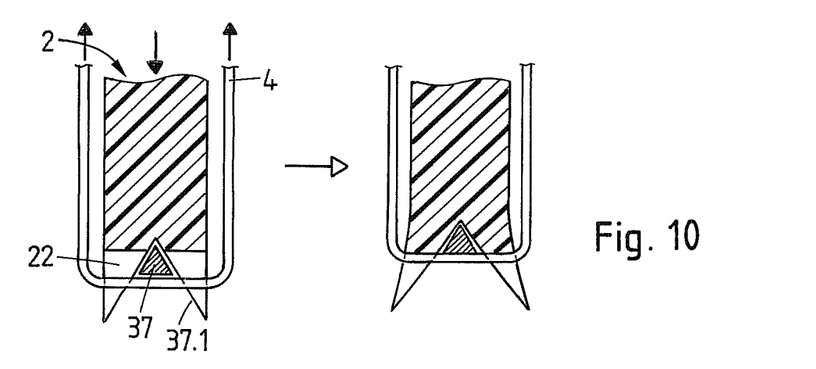

FIGS. 8 to 10 show exemplary embodiments of distal ends of suture anchors 2 comprising distal anchor sections 2.1 and 2.2 on either side of the distal portion of the suture groove 22 (undercut or not undercut) which distal anchor sections are forced apart and therewith pressed against the walls of the hard tissue opening such producing an additional press fit or positive fit by compressing the tissue of these walls during or possibly before the anchoring process. The distal anchor sections 2.1 and 2.2 are forced apart by the suture running through the distal groove 22 being pulled in a proximal direction (through exterior suture tension or through friction between the suture and the wall of the opening during advancement of the anchor into the hard tissue opening) and forced into the groove bottom, possibly assisted by a corresponding anchor design and/or a softening effect of the energy transmitted into the anchor for the liquefaction process.

FIGS. 8 to 10 are very schematic axial sections through distal end portions of suture anchors 2 comprising a suture groove 22 extending at an angle (preferably a right angle) to the anchor axis and separating the distal anchor portion into two distal sections 2.1 and 2.2. On the left hand side of the figures, a suture 4 is held in the suture groove 22, the suture not being tensioned (pulled in a proximal direction) or not tensioned enough for being able to deform the distal anchor portion, and on the right hand side of the figures, the suture 4 is tensioned and moved in a proximal direction therewith forcing apart or spreading the distal anchor sections 2.1 and 2.2.

FIG. 8 shows in addition a pair of transversal bores 36 orientated parallel to the distal suture groove 22 and situated underneath the groove bottom for weakening the corresponding anchor portion and therewith allowing the suture under tension, and possibly with the anchor material further weakened by the energy transferred into it for the liquefaction process, to be pulled into the suture material of the groove bottom and therewith spreading the lateral suture sections apart as shown on the right hand side of FIG. 8.

FIG. 9 shows an undercut distal suture groove 22 and an additional spreader element 37 located in the suture groove underneath the suture and having e.g. the form of a wedge. The spreader element 37 which preferably consists of a harder material or of a material with a higher melting or softening temperature than the suture anchor 2 is able to cut into the anchor material when forced against the bottom of the suture groove 22 by the tensioned suture.

FIG. 10 shows the distal suture groove 22 and the suture 4 running through the latter. The suture groove 22 and the suture 4 extend at an angle (preferably a right angle) to the spreader element 37 for which a further groove 37.1 is provided. The two grooves 22 and 37.1 separate the distal anchor portion into four sections wherein the two sections on the one side of the spreader groove 37.1 are forced apart from the two sections on the other side of the spreader groove by the spreader element 37 being forced into the bottom of the spreader groove 37.1 by the suture being tensioned, and wherein the two sections on the one side of the suture groove 22 may in addition be forced apart from the two sections on the other side of the suture groove, if the tensioned suture is also forced into the bottom of the suture groove 22.

Figure 11:
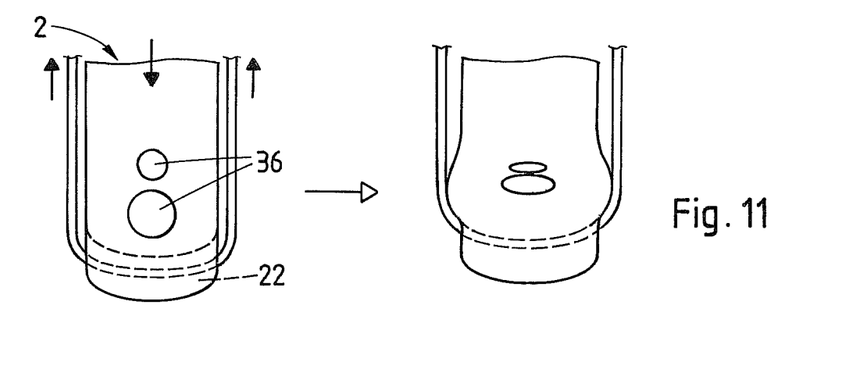

FIG. 11 illustrates the additional expansion by collapse of an anchor portion caused by the suture tension and/or by the distal anchor end being pushed against the bottom of the hard tissue opening. The anchor 2 comprises again a distal suture groove 22 and at least one (e.g. two) transversal bore 36 extending through the anchor 2 in a direction angled relative to the suture groove 22. The transversal bores 36, which cannot serve as a sort of perforation of the distal anchor portion as discussed in connection with FIGS. 18 and 19, form thin material portions which locally initiate absorption of the vibration such weakening the corresponding anchor portion and enabling collapse of the transversal bores and therewith local expansion of the anchor as shown on the right hand side of FIG. 11.

Figure 12:
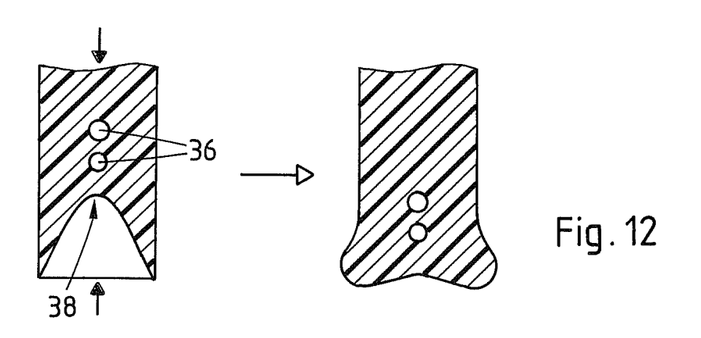

FIG. 12 illustrates in the same manner as FIGS. 8 to 11, a further measure for enhancing suture anchor retainment in bone tissue of an only limited mechanical strength, in particular in a blind opening of such a bone tissue. For enhancing softening and liquefaction in the distal anchor face even with very little counteraction by the bottom wall of the opening, the distal anchor end portion comprises thin and therewith mechanically weak portions of the material having thermoplastic properties, which weak portions tend to get softened or liquefied under the influence of the vibration used for the fixation process with hardly any friction on a counter element which in the present case is the bone tissue. This measure results in a collapse and therewith slight radial expansion of the distal anchor end portion and/or in a good penetration of the bone tissue situated around the distal anchor end portion, which may take over a main part of the anchoring function such that for lateral anchorage necessary friction on the lateral wall of the hard tissue opening may be reduced to a minimum.

Good results in corresponding experiments were achieved with distal anchor faces 38 of a concave shape (e.g. hollow cone or frustum as shown in FIG. 12), but can also be achieved with distal anchor faces with other hollow shapes, possibly additionally slotted or with distal anchor sections separated by grooves (e.g. suture groove) as shown in several previous Figures. The distal end of the suture anchor according to FIG. 12 additionally comprises two (or more than two) transversal bores 36 serving as weakening structures as discussed in connection with FIGS. 8, 9, and 11 and/or as possibly collapsible suture conduits.

All the measures illustrated in FIGS. 8 to 12 are applicable e.g. in anchors as previously described. However, they are also applicable in anchors having other characteristics. For this reason, the invention also concerns an anchor (preferably suture anchor) and a method for fixating the anchor in a hard tissue opening comprising only the features as disclosed in FIGS. 8 to 12 and serving for enhancing anchor retainment in the hard tissue opening. The corresponding anchor is characterized by a distal end portion comprising end sections separated by a groove, by a concave distal face, or by a weakened anchor portion proximally adjoining a distal suture conduit. The corresponding method is characterized by spreading the end sections, or by collapsing and therewith expanding the weakened anchor portion, the concave distal face or the end sections through tensioning of the suture or through abutting the anchor against the bottom of a blind hard tissue opening.

In the above described embodiments, according to FIGS. 8 to 11, the suture being fixated relative to hard tissue may have a specific function (spreading or expanding a distal anchor portion) in the method according to which the suture anchor is fixated in the hard tissue. If these embodiments of anchors are to be used in other applications than as suture anchors or in combination with sutures which are mechanically too weak for the named functions, it is possible to make use of a suture substitute, to position and use this suture substitute instead of or in addition to the suture as described and to finally remove it or clip end portions of it. Such suture substitutes may be any flexible and elongated item such as e.g. a wire, a ribbon or a suture of suitable characteristics. The term "suture" as used in the above description encompasses such suture substitutes.

The above described invention concerns in particular suture anchors suitable for soft tissue attachment to hard tissue. In all the described embodiments of methods for fixating such suture anchors in hard tissue, the sutures may be further safeguarded against damage by heat dissipating from the material having thermoplastic properties when liquefied, by being soaked with liquid (water or saline solution) preferably before being threaded through the distal suture conduit or before being positioned in the hard tissue opening and necessarily before liquefaction of the material having thermoplastic properties.

In all above described methods for attaching soft tissue to hard tissue with the aid of a suture anchor and a suture, a material having thermoplastic properties is liquefied to preferably penetrate hard tissue or cavities provided in the hard tissue to constitute when re-solidified a positive-fit connection between the anchor or part thereof and the hard tissue of the wall of the opening. Such positive fit connections can in all described cases be achieved also in a two-step procedure, wherein the walls of the hard tissue opening are pre-treated according to a method as described in the publications WO-2010/045751 or WO-2009/141252 (Nexilis), wherein a material having thermoplastic properties is forced in a liquefied state into the hard tissue of the wall of the opening to form together with this tissue a sort of composite substantially without coating this wall with the material having thermoplastic properties. In a second step the anchoring process is then carried out as described in the present description and in the cited publications, wherein the liquefied material is not able to penetrate the composite material of the wall of the opening established in the pre-treatment step, but instead is welded to the composite material of this wall. For such welding it is a condition that the material having thermoplastic properties used in the second or fixation step is weldable to the material having thermoplastic properties used in the first or pre-treatment step. Preferably the two materials having thermoplastic properties comprise the same thermoplastic polymer.

If the named pre-treatment step is carried out in a manner to form the composite material comprising the hard tissue and the material having thermoplastic material right to the mouth of the hard tissue opening, this mouth is strengthened and therewith has an enhanced capacity to resist being cut by the suture fixated in the hard tissue opening by the anchor fixated therein, when this suture is tensioned.

What is claimed is:

1. A kit of parts comprising:
    a suture anchor and a tool;
    the tool being suitable for fixating the suture anchor in a hard tissue opening by positioning a distal tool face against a proximal anchor face;
    wherein the tool is a vibration tool equipped to be coupled to an ultrasonic vibration generator and to be set into ultrasonic vibration;
    wherein the distal tool face is a distally facing distal vibration outcoupling face shaped to be positioned against the proximal anchor face for transmitting the ultrasonic vibration from the tool into the suture anchor;
    wherein the proximal anchor face comprises at least two mouths of suture grooves extending in an axial direction along a circumferential surface of the suture anchor;
    wherein a distal portion of the tool comprises lateral grooves each having a lateral groove mouth in the distal tool face;
    wherein the tool has a single distal alignment protrusion protruding distally from the distal tool face, the alignment protrusion having an elongate rectangular transverse section and being tapered, wherein the anchor comprises a depression in the proximal anchor face, the depression being shaped corresponding to a shape of the alignment protrusion, whereby introduction by axial pushing of the alignment protrusion into the depression results automatically in a proper alignment of the lateral groove mouths with the at least two mouths of the suture grooves, whereby the distal tool face does not cover the at least two mouths of the suture grooves;
    wherein the suture anchor comprises a material having thermoplastic properties being liquefiable, where in contact with the hard tissue when inserted in the hard tissue opening, by the ultrasonic vibration transmitted from the tool to the suture anchor, whereby the kit is equipped for the suture anchor to be anchored in the hard tissue opening by transmission of a pushing force and mechanical vibration from the tool to the suture anchor to cause at least a portion of the material having thermoplastic properties to liquefy and to penetrate into structures of the hard tissue to yield, after re-solidification of the portion, an anchoring therein.

2. The kit according to claim 1, wherein the tool comprises at least two lateral grooves, and the suture anchor comprises the at least two suture grooves, wherein each suture groove comprises a mouth in the proximal anchor face,
    wherein the distal tool face and the proximal anchor face are adapted to each other such that
        the distal tool face does not cover a first mouth of a first suture groove comprised by the proximal anchor face, when the distal tool face is positioned against the proximal anchor face for the fixation process, and
        the distal tool face does not cover a second mouth of a second suture groove comprised by the proximal anchor face, when the distal tool face is positioned against the proximal anchor face for the fixation process.

3. The kit according to claim 1, wherein the distal tool face and the proximal anchor face have different shapes such that a portion of the proximal anchor face in which the at least two mouths are situated protrudes from the distal tool face when the distal tool face is positioned against the proximal anchor face for the fixation process.

4. The kit according to claim 1, wherein the distal tool face and the proximal anchor face have different shapes such that a portion of the distal tool face protrudes from the proximal anchor face in which the at least two mouths are situated when the distal tool face is positioned against the proximal anchor face for the fixation process.

5. The kit according to claim 1, wherein the distal tool face is circular and the proximal anchor face is oblong.

6. The kit according to claim 1, wherein the suture anchor comprises at least one distal suture conduit being collapsible for locking the suture relative to the fixated anchor.

7. A suture anchoring kit, comprising:
    a suture anchor for being anchored in a hard tissue opening, the suture anchor having a proximal anchor face and comprising a material having thermoplastic properties being liquefiable;

a vibration generator of ultrasonic vibration, the vibration generator being a piezoelectric vibration;

and a tool having a distal tool face being a distally facing distal vibration outcoupling face shaped to be positioned against the proximal anchor face, the tool being equipped to be coupled to the vibration generator and to transmit the ultrasonic vibration from the vibration generator to the suture anchor via the distal tool face by the distal tool face being positioned against the proximal anchor face;

wherein the proximal anchor face comprises at least two mouths of suture grooves extending in an axial direction along a circumferential surface of the suture anchor;

wherein the suture anchor further comprises at least one distal suture conduit, the suture conduit running from one lateral side of the suture anchor to another lateral side thereof, the suture conduit being a distal suture groove, a distal suture channel or a distal eyelet, the suture conduit being collapsible for locking the suture relative to the suture anchor when the suture anchor is anchored in the hard tissue opening;

wherein a distal portion of the tool comprises lateral grooves each having a lateral groove mouth in the distal vibration outcoupling face;

wherein the tool has a single distal alignment protrusion protruding distally from the vibration outcoupling face, the alignment protrusion having an elongate rectangular transverse section and being tapered, wherein the anchor comprises a depression in the proximal anchor face, the depression shaped corresponding to a shape of the alignment protrusion, whereby introduction by axial pushing of the alignment protrusion into the depression results automatically in a proper alignment of the lateral groove mouths with the at least two mouths of the suture grooves;

wherein the material having thermoplastic properties is liquefiable where in contact with the hard tissue when inserted in the hard tissue opening by the ultrasonic vibration transmitted from the tool to the suture anchor, whereby the kit is equipped for the suture anchor to be anchored in the hard tissue opening by transmission of a pushing force and mechanical vibration from the vibration generator via the tool to the suture anchor to cause at least a portion of the material having thermoplastic properties to liquefy and to penetrate into structures of the hard tissue to yield, after re-solidification of the portion, an anchoring therein.

* * * * *